United States Patent
Miyamoto et al.

(10) Patent No.: US 11,934,246 B2
(45) Date of Patent: Mar. 19, 2024

(54) POWER SUPPLY DEVICE, ELECTROMEDICAL DEVICE SYSTEM, RELAY DEVICE, AND METHOD OF CONTROLLING POWER SUPPLY DEVICE

(71) Applicant: Japan Lifeline Co., Ltd., Tokyo (JP)

(72) Inventors: Hisao Miyamoto, Tokyo (JP); Yusuke Oshima, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 69 days.

(21) Appl. No.: 17/941,759

(22) Filed: Sep. 9, 2022

(65) Prior Publication Data
US 2023/0205298 A1    Jun. 29, 2023

(30) Foreign Application Priority Data
Dec. 27, 2021 (JP) ................ 2021-212613

(51) Int. Cl.
*G06F 1/32* (2019.01)
*G06F 1/3206* (2019.01)
*G06F 1/3287* (2019.01)

(52) U.S. Cl.
CPC .......... *G06F 1/3206* (2013.01); *G06F 1/3287* (2013.01)

(58) Field of Classification Search
CPC . G06F 1/3206; G06F 1/3287; A61B 18/1477; A61B 18/148; A61B 18/1233; A61B 18/1492; A61B 2018/00601; A61B 2018/00702; A61B 2018/00708; A61B 2018/00577; A61B 2018/00642; A61B 2018/00875; A61B 2018/167
See application file for complete search history.

(56) References Cited

U.S. PATENT DOCUMENTS

| 10,631,913 | B2 | 4/2020 | Hull et al. |
| 2010/0052420 | A1* | 3/2010 | Kang .............. H02J 9/005 307/31 |
| 2012/0323236 | A1* | 12/2012 | Hagg .............. A61B 18/1233 606/41 |
| 2021/0243046 | A1* | 8/2021 | Tada .............. H04L 12/40013 |

FOREIGN PATENT DOCUMENTS

| JP | 2018501874 A | 1/2018 |
| WO | WO2020/198796 | 10/2020 |

* cited by examiner

*Primary Examiner* — Nitin C Patel
(74) *Attorney, Agent, or Firm* — MUNCY, GEISSLER, OLDS & LOWE, PC

(57) ABSTRACT

Object
Provided is a power supply device and the like capable of improving convenience.
Solving means
A power supply device according to an embodiment of the present disclosure include a power supply unit that supplies power to an electromedical device, a first impedance control unit disposed on a path of a circulation path of the power between the power supply unit and the electromedical device, excluding an input path for inputting an electrical signal obtained in the electromedical device to another device, and a second impedance control unit disposed on the input path of a path between the power supply unit and the other device. An impedance state of each of the first and second impedance control units transitions in accordance with a supply state of the power to the electromedical device.

14 Claims, 11 Drawing Sheets

| | Pout SUPPLY STATE (ENERGIZATION STATE) | |
|---|---|---|
| | POWER SUPPLY PERIOD Te | POWER STOP PERIOD Tn |
| RELAY 341 | ON STATE (LOW IMPEDANCE STATE) | OFF STATE (HIGH IMPEDANCE STATE) |
| RELAY 342 | OFF STATE (HIGH IMPEDANCE STATE) | ON STATE (LOW IMPEDANCE STATE) |

FIG. 2

MODIFIED EXAMPLE 2

|  | Pout SUPPLY STATE (ENERGIZATION STATE) ||
| --- | --- | --- |
|  | POWER SUPPLY PERIOD Te | POWER STOP PERIOD Tn |
| LC RESONANT CIRCUIT 341B | LOW IMPEDANCE STATE | HIGH IMPEDANCE STATE |
| LC RESONANT CIRCUIT 342B | HIGH IMPEDANCE STATE | LOW IMPEDANCE STATE |

FIG. 8

POWER SUPPLY DEVICE, ELECTROMEDICAL DEVICE SYSTEM, RELAY DEVICE, AND METHOD OF CONTROLLING POWER SUPPLY DEVICE

TECHNICAL FIELD

The present disclosure relates to a power supply device, an electromedical device system, a relay device, and a method of controlling the power supply device.

BACKGROUND ART

For example, Patent Literature 1 discloses an electromedical device system including an electromedical device, such as an ablation catheter, and a power supply device that supplies power to the electromedical device.

CITATION LIST

Patent Literature

Patent Literature 1: JP 2018-501874 T

SUMMARY OF INVENTION

Technical Problem

However, there is typically a demand for improved convenience when using an electromedical device system and the like. It is desirable to provide a power supply device, an electromedical device system, a relay device, and a method of controlling the power supply device that are capable of improving convenience.

Solution to Problem

A first power supply device according to an embodiment of the present disclosure includes a power supply unit that supplies power to an electromedical device, a first impedance control unit disposed on a path of a circulation path of the power between the power supply unit and the electromedical device, excluding an input path for inputting an electrical signal obtained in the electromedical device to another device, and a second impedance control unit disposed on the input path of a path between the power supply unit and the other device. An impedance state of each of the first and second impedance control units transitions in accordance with a supply state of the power to the electromedical device.

A second power supply device according to an embodiment of the present disclosure includes a first supply unit that supplies power from a power supply unit to an electromedical device, and a second supply unit that supplies an electrical signal obtained in the electromedical device to another device. A transition is made, in accordance with a supply state of the power to the electromedical device, between a power supply state in which the other device is electrically separated from the first supply unit and the power is supplied to the first supply unit and a power stop state in which the electrical signal is supplied to the second supply unit and the second supply unit is electrically separated from other portions.

An electromedical device system according to an embodiment of the present disclosure includes an electromedical device, and the first or second power supply device according to the embodiment of the present disclosure that supplies power to the electromedical device.

A relay device according to an embodiment of the present disclosure is a device for relaying between an electromedical device and a power supply device that supplies power to the electromedical device, the relay device including a first impedance control unit disposed on a path of a circulation path of the power between the power supply device and the electromedical device, excluding an input path for inputting an electrical signal obtained in the electromedical device to another device, and a second impedance control unit disposed on the input path of a path between the power supply device and the other device. An impedance state of each of the first and second impedance control units transitions in accordance with a supply state of the power to the electromedical device.

A method of controlling a power supply device according to an embodiment of the present disclosure is a method of controlling a power supply device including a first supply unit that supplies power from a power supply unit to an electromedical device, and a second supply unit that supplies an electrical signal obtained in the electromedical device to another device, the method including making a transition, in accordance with a supply state of the power to the electromedical device, between a power supply state in which the other device is electrically separated from the first supply unit and the power is supplied to the first supply unit and a power stop state in which the electrical signal is supplied to the second supply unit and the second supply unit is electrically separated from other portions.

BRIEF DESCRIPTION OF DRAWINGS

FIG. 2 is a diagram illustrating an example of a transition mode of an impedance state of each relay illustrated in FIG. 1.

FIG. 8 is a diagram illustrating an example of a transition mode of an impedance state of each LC resonant circuit illustrated in FIG. 7.

DESCRIPTION OF EMBODIMENT

An embodiment of the present disclosure will be described below in detail with reference to the drawings. Note that the description will be given in the following order.
1. Embodiment (example in which each impedance control unit includes a relay)
2. Modified Examples
   Modified Example 1 (example in which an impedance is measured in a low voltage output period)
   Modified Example 2 (example in which each impedance control unit includes an LC resonant circuit)
   Modified Example 3 (example of another arrangement configuration of a first impedance control unit)
   Modified Examples 4 and 5 (examples when each impedance control unit is disposed in a relay device)
3. Other Modified Examples

1. EMBODIMENT

Configuration of Electromedical Device System 5

Figure 1:
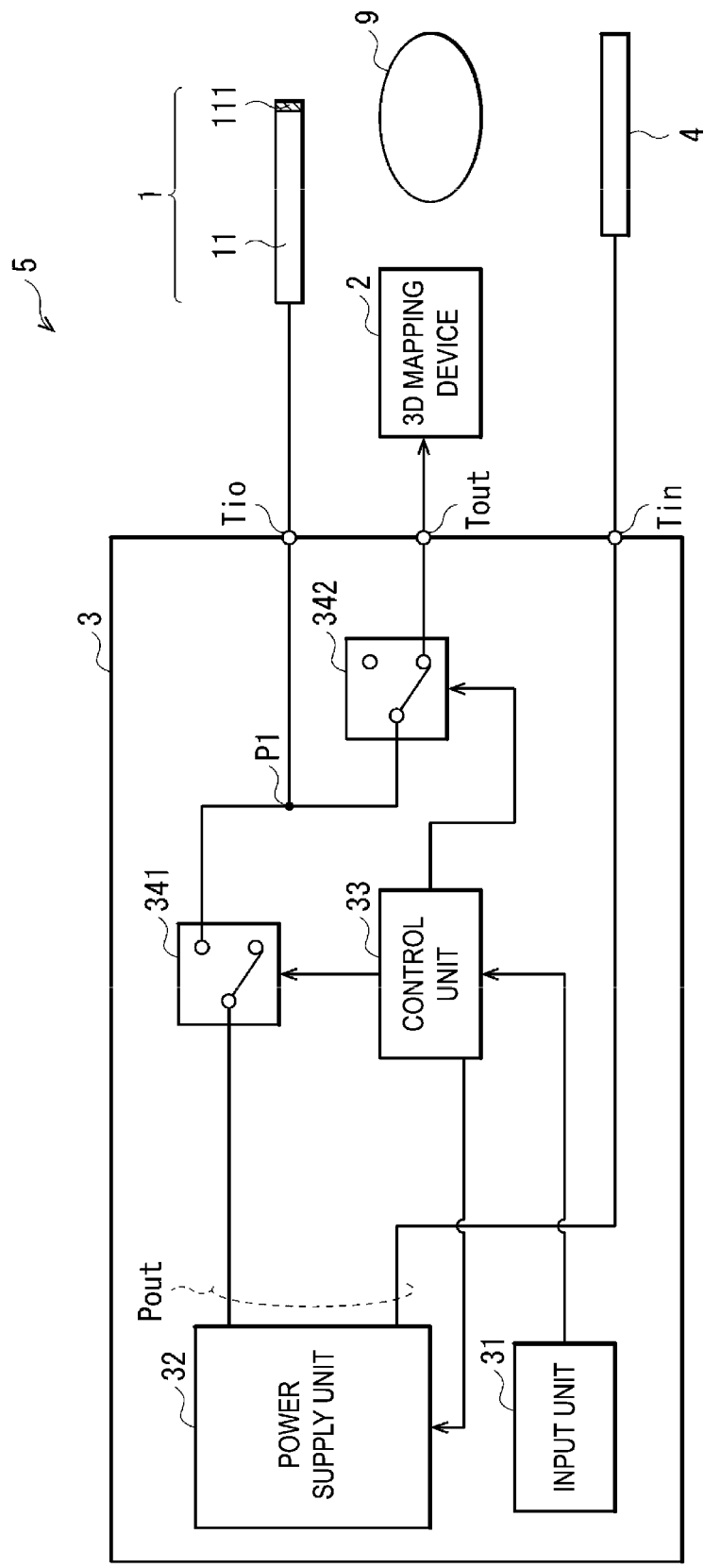
FIG. 1 is a block diagram schematically illustrating an overall configuration example of an electromedical device system according to an embodiment of the present disclosure.

FIG. 1 is a block diagram schematically illustrating an overall configuration example of an electromedical device system 5 according to an embodiment of the present disclosure. The electromedical device system 5 is a system used in performing a treatment or the like in a body of a patient 9. The treatment or the like includes treatment such as ablation on the affected area, incision and the like. Since a "method of controlling a power supply device" in the present disclosure is embodied in the electromedical device system of the present disclosure, the method will be described together below.

The electromedical device system 5 includes an electromedical device 1, a 3D mapping device 2 and a power supply device 3, as illustrated in FIG. 1. In performing the treatment or the like using the electromedical device system 5, a counter electrode plate 4 illustrated in FIG. 1 is also used as appropriate.

Electromedical Device 1

The electromedical device 1 is a device used in performing the treatment or the like described above, and includes a device body 11 and an electrode 111. The electromedical device 1 includes, for example, an ablation catheter, an electrode needle, and an electrical scalpel.

The electrode 111 is disposed near the distal end of the elongated device body 11. The single electrode 111 is provided on the device body 11. In the example of FIG. 1, the electrode 111 is provided near the distal end of the device body 11. Power Pout is supplied from the electrode 111 toward the counter electrode plate 4, and the treatment or the like is performed. The electromedical device 1 utilizes the electrodes 111 to acquire potential information of the heart of the patient 9 and position information of the electrode 111. The potential information and the position information are output from the electromedical device 1 as an electrical signal (three-dimensional mapping signal Sd).

3D Mapping Device 2

The 3D mapping device 2 outputs the electrical signal (three-dimensional mapping signal Sd) obtained by the electromedical device 1 to the outside by displaying the signal in 3D (three dimensions). The three-dimensional mapping signal Sd is input from the electromedical device 1 into the power supply device 3 via an input/output terminal Tio, and is input from the power supply device 3 to the 3D mapping device via an output terminal Tout. The 3D mapping device 2 corresponds to a specific example of a "mapping device" in the present disclosure.

Power Supply Device 3

The power supply device 3 supplies power Pout (for example, radio frequency (RF) power) for performing the treatment or the like between the electrode 111 and the counter electrode plate 4. That is, the power supply device 3 supplies the power Pout to the electromedical device 1. The power supply device 3 includes an input unit 31, a power supply unit 32, a control unit 33, and relays 341 and 342.

The input unit 31 is a portion that outputs an instruction signal (operation signal) for indicating various types of setting values or predetermined operations. The operation signal is output from the input unit 31 to the control unit 33 in response to an operation on a button or the like by an operator (for example, a technician) of the power supply device 3. However, various setting values may be set in the power supply device 3 in advance, for example, when the product is shipped, rather than being input in response to the operation by the operator.

The power supply unit 32 outputs the power Pout according to the control by the control unit 33. The power supply unit 32 includes a predetermined power supply circuit (for example, a switching regulator). For example, when the power Pout is radio frequency power, the frequency of the power Pout is approximately 450 kHz to 550 kHz (suitably 500 kHz).

The control unit 33 is a unit that controls the entire power supply device 3 and performs predetermined arithmetic processing, and includes, for example, a microcomputer. The control unit 33 controls the supply operation of the power Pout from the power supply unit 32, for example. Further, the control unit 33, which will be described later in detail (FIGS. 2 to 4), performs switching control of the impedance state (ON state or OFF state described below) of each of the relays 341 and 342 in accordance with the state of energizing an energization target (the affected area of the patient 9) from the electromedical device 1. In other words, the control unit 33 transitions the impedance state of each of the relays 341 and 342 in accordance with the supply state of the power Pout from the power supply unit 32 to the electromedical device 1. In other words, the control unit 33 corresponds to a specific example of a "relay control unit" in the present disclosure.

Each of the relays 341 and 342 is an element switching between the connected state (ON state) and the non-connected state (OFF state) between the contacts on the path in accordance with the control from the control unit 33. In other words, the impedance state (between contacts) of each of the relays 341 and 342 transitions (switches) between a low impedance state (ON state) and a high impedance state (OFF state). In the example illustrated in FIG. 1, the relays 341 and 342 are configured by double-pole double-throw relays that operate in conjunction with each other.

The relay 341 is disposed on a path of the circulation path of the power Pout (for example, RF signal) between the power supply unit 32 and the electromedical device 1, excluding the input path of the three-dimensional mapping signal Sd to the 3D mapping device 2. Here, the input path of the three-dimensional mapping signal Sd means the path from the electromedical device 1 to the 3D mapping device 2 via the input/output terminal Tio, the connection point P1, and the output terminal Tout. Specifically, the relay 341 is disposed on a path, excluding the input path from the connection point P1 to the electrode 111, of the circulation path (the path Rp described later) from the power supply unit 32 to the power supply unit 32 via the connection point P1, the input/output terminal Tio, the electrode 111 on the electromedical device 1, the energization target (the affected area of the patient 9), the counter electrode plate 4, and the input terminal Tin. Specifically, in the example illustrated in FIG. 1, the relay 341 is disposed between the power supply unit 32 and the electromedical device 1 (between the power supply unit 32 and the connection point P1 between the power supply unit 32 and the input/output terminal Tio) on a path of the circulation path excluding the input path. A circuit including the circulation path corresponds to a specific example of a "first supply unit (that supplies power from a power supply unit to an electromedical device)" in the present disclosure.

Of the path between the power supply unit 32 and the 3D mapping device 2, the relay 342 is disposed on the above-described input path of the three-dimensional mapping signal Sd. Specifically, the relay 342 is disposed between the connection point P1 and the output terminal Tout described above on the input path. That is, the arrangement position of the relay 342 is not on the path between the arrangement position of the relay 341 and the connection point P1. A circuit including the input path corresponds to a specific example of a "second supply unit (that supplies an electrical signal obtained in the electromedical device to another device)" in the present disclosure.

The relay 341 corresponds to specific examples of a "first impedance control unit" and a "first relay" in the present disclosure. The relay 342 corresponds to specific examples of a "second impedance control unit" and a "second relay" in the present disclosure.

Counter Electrode Plate 4

The counter electrode plate 4 is used in a state of being attached to the body surface of the patient 9 when a treatment or the like is performed. When the treatment or the like is performed, radio frequency energization is performed between the electrode 111 and the counter electrode plate 4 (the power Pout is supplied).

Operation and Advantages and Effects

A. Basic Operation

In the electromedical device system 5, a treatment or the like is performed on the affected area of the patient 9. In performing the treatment or the like, the device body 11 is inserted into the body of the patient 9 from its distal end. The power Pout (for example, radio frequency power) is supplied between the electrode 111 near the distal end of the device body 11 and the counter electrode plate 4 from the power supply device 3, so that the treatment or the like by the Joule heat generation is performed on the affected area in the body of the patient 9.

B. Switching Operation of Relays 341 and 342

Figure 3:
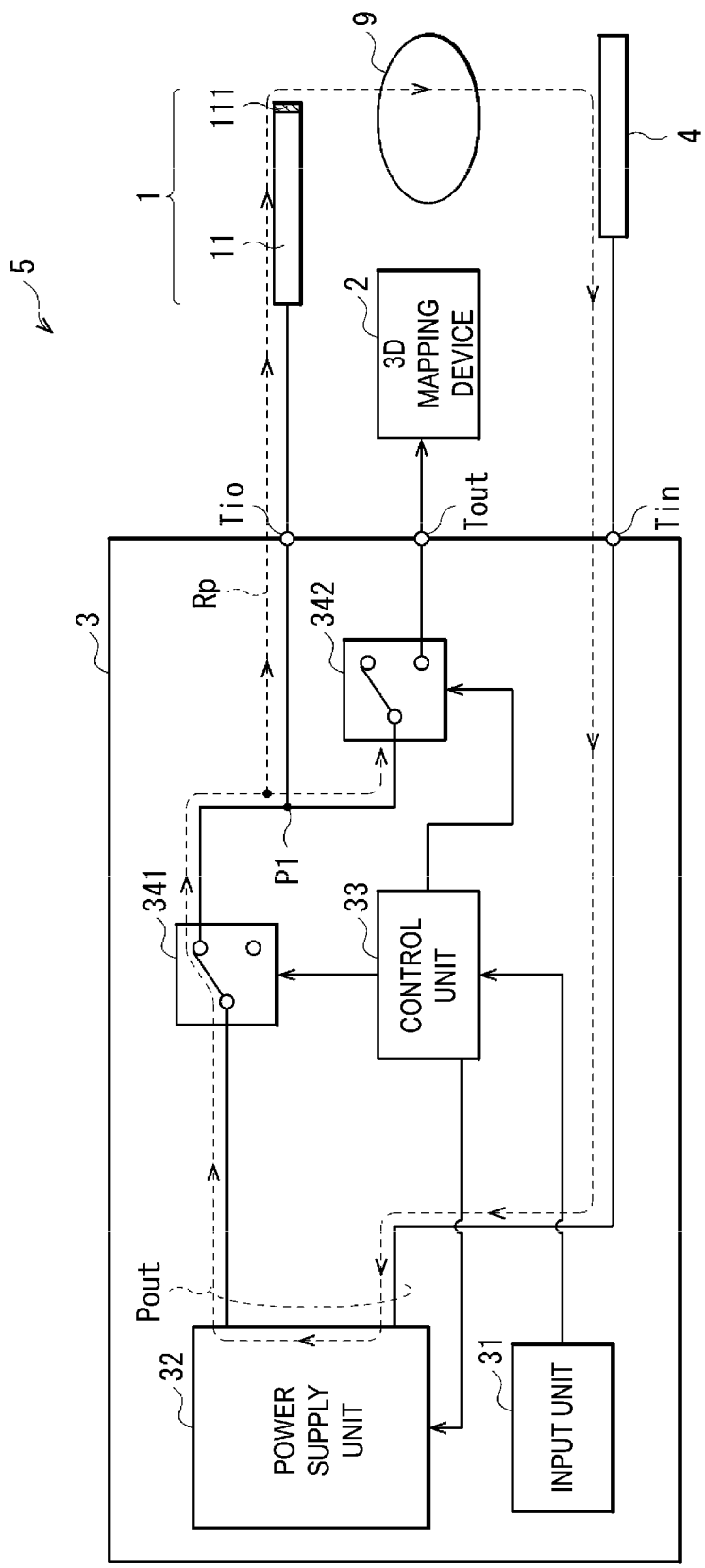
FIG. 3 is a block diagram illustrating an example of a state of the electromedical device system illustrated in FIG. 1 in a power supply period.
Figure 4:
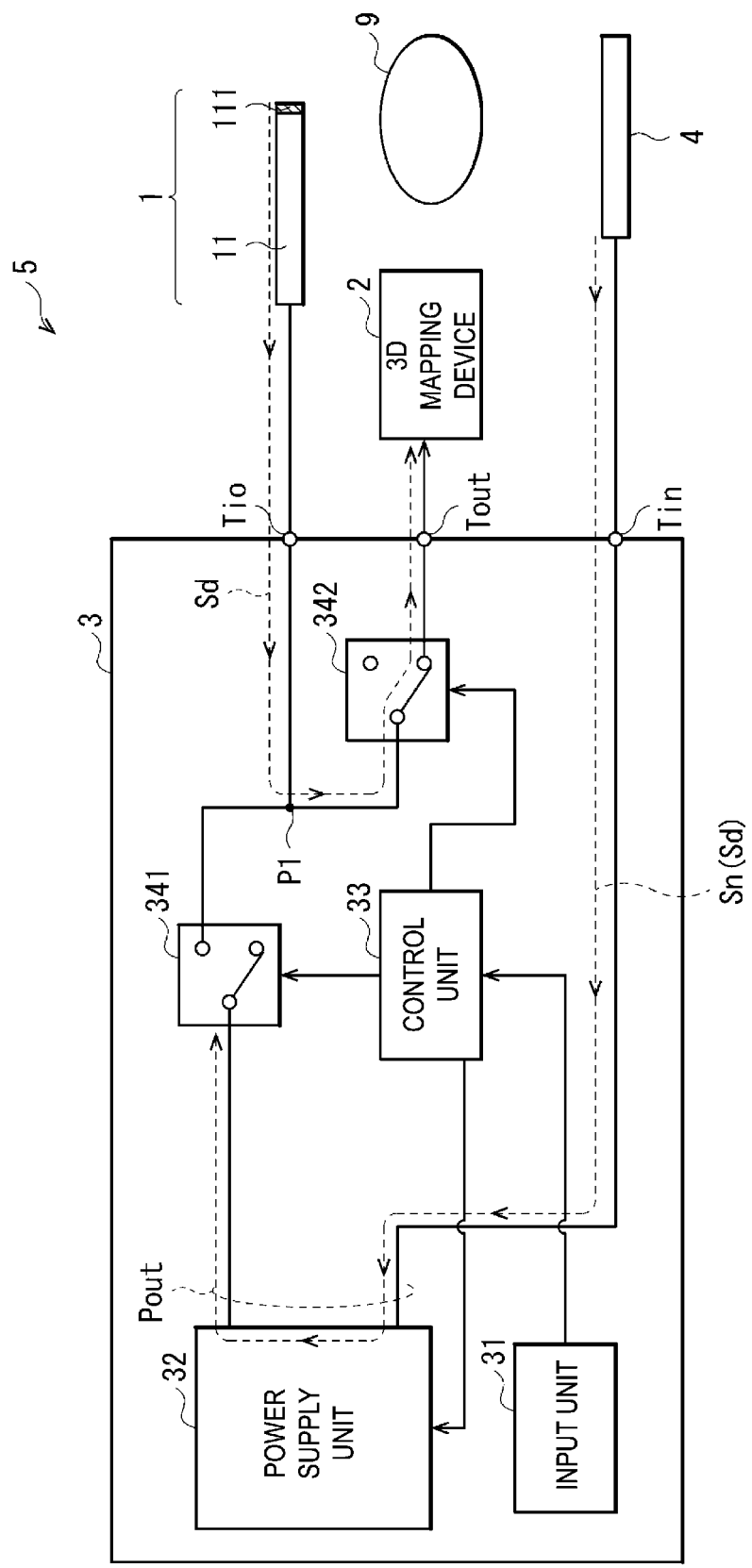
FIG. 4 is a block diagram illustrating an example of a state of the electromedical device system illustrated in FIG. 1 in a power stop period.

Referring now to FIGS. 2 to 4, a switching operation (a transition operation) of the impedance state (ON state or OFF state) of each of the relays 341 and 342 will be described in detail. Specifically, the switching control of the impedance state of each of the relays 341 and 342 by the control unit 33 will be described in particular in the present embodiment.

FIG. 2 illustrates an example of a transition mode (switching mode) of the impedance state of each of the relays 341 and 342. FIG. 3 is a block diagram illustrating an example of a state (power supply state) of the electromedical device system 5 in a power supply period Te, which is a period of energization (during the supply of the power Pout). FIG. 4 is a block diagram illustrating an example of a state (power stop state) of the electromedical device system 5 in a power stop period Tn, which is a period of non-energization (during stopping of the supply of the power Pout).

As illustrated in FIG. 2, the impedance state of each of the relays 341 and 342 transitions according to the supply state of the power Pout (the state of energizing the energization target (the affected area of the patient 9)). In particular, in the present embodiment, the control unit 33 performs switching control between the ON states and the OFF states of the relays 341 and 342 as the impedance states of the relays 341 and 342 according to the supply state of the power Pout. The switching control for each of the relays 341 and 342 is automatically performed by the control unit 33, for example, using a predetermined power supply start signal (energization start signal) as a trigger.

B-1. Power Supply Period Te

Specifically, in the power supply period Te, the relay 341 is in a low impedance state and the relay 342 is in a high impedance state (a state in which the impedance is higher than the impedance in the low impedance state) (FIG. 2). That is, as illustrated in FIGS. 2 and 3, for example, the control unit 33 performs switching control in the power supply period Te such that the relay 341 becomes in an ON state (low impedance state), and the relay 342 becomes in an OFF state (high impedance state).

In this way, in the power supply period Te, the power Pout is supplied from the power supply unit 32 (energizing the energization target (the affected area of the patient 9)) on the path Rp indicated by the dashed line in FIG. 3, for example. In particular, the path Rp is a circulation path from the power supply unit 32 to the power supply unit 32 via the connection point P1, the input/output terminal Tio, the electrode 111 on the electromedical device 1, the energization target, the counter electrode plate 4, and the input terminal Tin. Since the relay 342 is in the OFF state at this time, it is avoided that the power Pout (RF signal) from the path Rp is input to the 3D mapping device 2 via the relay 342. That is, in the power supply period Te, the 3D mapping device 2 is in a state (power supply state) of being electrically separated from the circuit including the power supply unit 32, the counter electrode plate 4, and the electromedical device 1. As a result, in the power supply period Te, the 3D mapping device 2 is protected (against the RF signal input).

B-2. Power Stop Period Tn

In contrast, in the power stop period Tn, the relay 341 is in a high impedance state, and the relay 342 is in a low impedance state (FIG. 2). That is, as illustrated in FIGS. 2 and 4, for example, the control unit 33 performs switching control in the power stop period Tn such that the relay 341 becomes in an OFF state (high impedance state), and the relay 342 becomes in an ON state (low impedance state).

In this way, in the power stop period Tn, as illustrated in FIG. 4, the relay 341 switches to the OFF state, and thus the supply (energization) of the power Pout from the power supply unit 32 is stopped. Additionally, in the power stop period Tn, as indicated by the dashed line in FIG. 4, the three-dimensional mapping signal Sd measured in the electrode 111 on the electromedical device 1 is input to the 3D mapping device 2 via the input/output terminal Tio, the connection point P1, the relay 342 (ON state), and the output terminal Tout in this order. Thus, in the 3D mapping device 2, 3D display based on the input three-dimensional mapping signal Sd is made.

In this case, even in the counter electrode plate 4, the three-dimensional mapping signal Sd is picked up as a noise signal Sn. In other words, as indicated by the dashed line in FIG. 4, the noise signal Sn (three-dimensional mapping signal Sd) is input from the counter electrode plate 4 into the power supply device 3 via the input terminal Tin and the power supply unit 32. However, in the power stop period Tn, since the relay 341 is in the OFF state, it is avoided that the noise signal Sn is input to the 3D mapping device 2 via the relay 342 in the ON state (the noise signal Sn is mixed into the original three-dimensional mapping signal Sd). That is, in the power stop period Tn, the 3D mapping device 2 is in a state (non-energization state) of being electrically separated from the circuit including the counter electrode plate 4 and the power supply unit 32 (corresponding to a specific example of a circuit constituting "other portions" in the present disclosure). As a result, in the power stop period Tn, error of the three-dimensional mapping signal Sd (error of measurement position) is reduced.

C. Advantages and Effects

In this way, in the present embodiment, the impedance state of each of the relays 341 and 342 (the power supply state and the power stop state of the power supply device 3) transitions in accordance with the supply state of the power Pout (the state of the energization), so that it is possible to achieve the following. That is, in the power supply period Te, the 3D mapping device 2 is protected, and in the power stop period Tn, the occurrence of error of the three-dimensional mapping signal Sd due to the noise signal Sn is avoided (error of the three-dimensional mapping signal Sd is reduced). As a result, in the present embodiment, the convenience when the electromedical device system 5 (the power supply device 3) is used can be improved.

In particular, in the present embodiment, the control unit 33 performs switching control between the ON state and the OFF state of each of the relays 341 and 342 according to the supply state of the power Pout, so that it is possible to achieve the following. That is, for example, the impedance state (ON state or OFF state) of each of the relays 341 and 342 can be switched independently of the frequency band or the like of the RF signal (power Pout) or the three-dimensional mapping signal Sd. As a result, the convenience can be further improved.

2. MODIFIED EXAMPLES

Next, modified examples (Modified Examples 1 to 5) of the above-described embodiment will be described. The same components as those in the embodiment are designated by the same reference numerals, and the description thereof will be omitted as appropriate.

Modified Example 1

Figure 5:
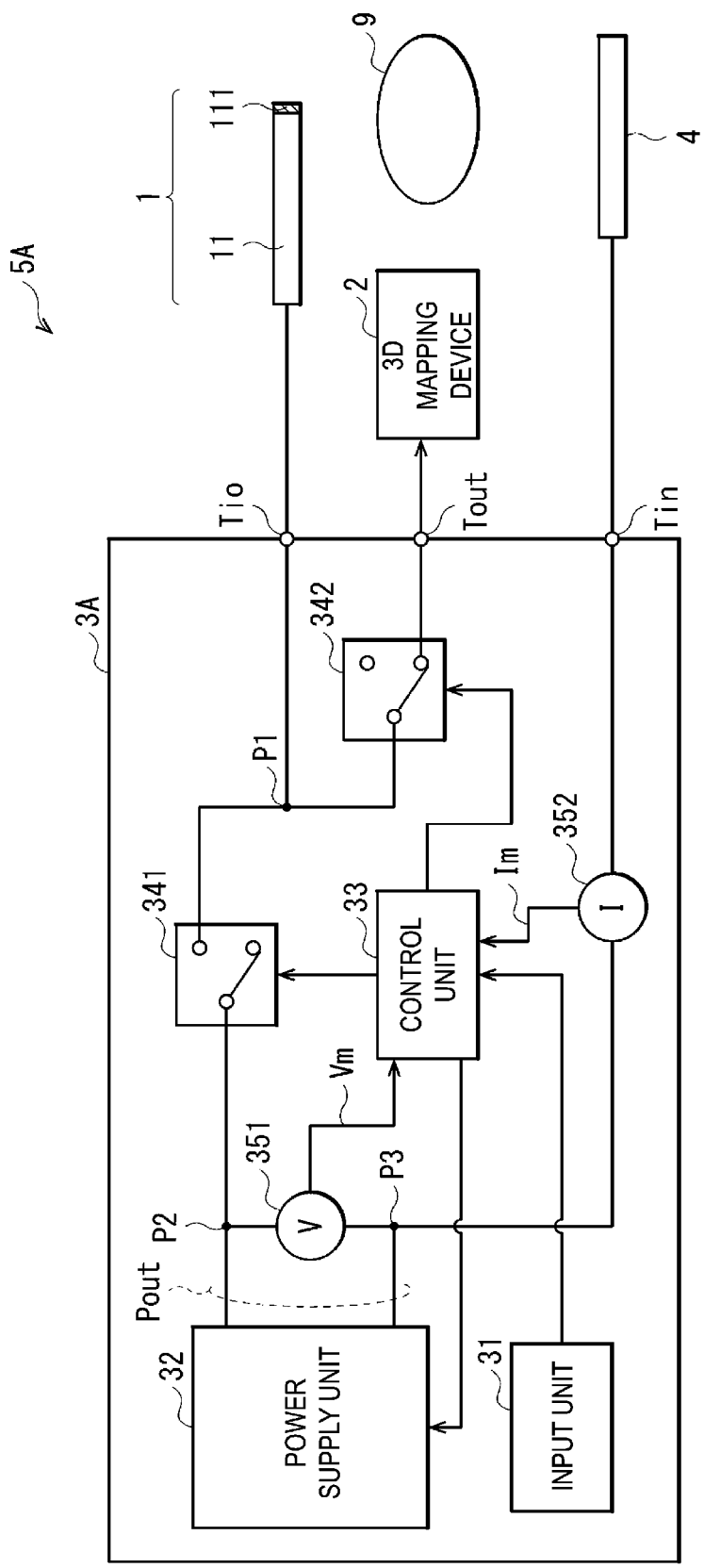
FIG. 5 is a block diagram schematically illustrating an overall configuration example of an electromedical device system according to Modified Example 1.

FIG. 5 is a block diagram schematically illustrating an overall configuration example of an electromedical device system 5A according to Modified Example 1. As to the electromedical device system 5A, a power supply device 3A is provided instead of the power supply device 3 in the electromedical device system 5 (FIG. 1) of the embodiment. The other configurations are the same.

As to the power supply device 3A, a voltage measurement unit 351 and a current measurement unit 352 are further provided in the power supply device 3 (FIG. 1). The other configurations are the same.

The voltage measurement unit 351 measures a potential difference (voltage) between the connection point P2 on the path between the power supply unit 32 and the relay 341 and the connection point P3 on the path between the input terminal Tin and the power supply unit 32, and outputs the potential difference as a measured voltage Vm.

The current measurement unit 352 measures a current flowing through the path between the input terminal Tin and the power supply unit 32, and outputs the current as measured current Im.

In Modified Example 1, the control unit 33 calculates an impedance value Zm (=Vm/Im) on the basis of the measured voltage Vm supplied from the voltage measurement unit 351 and the measured current Im supplied from the current measurement unit 352. In this manner, the impedance value Zm is measured in the electromedical device system 5A.

Figure 6:
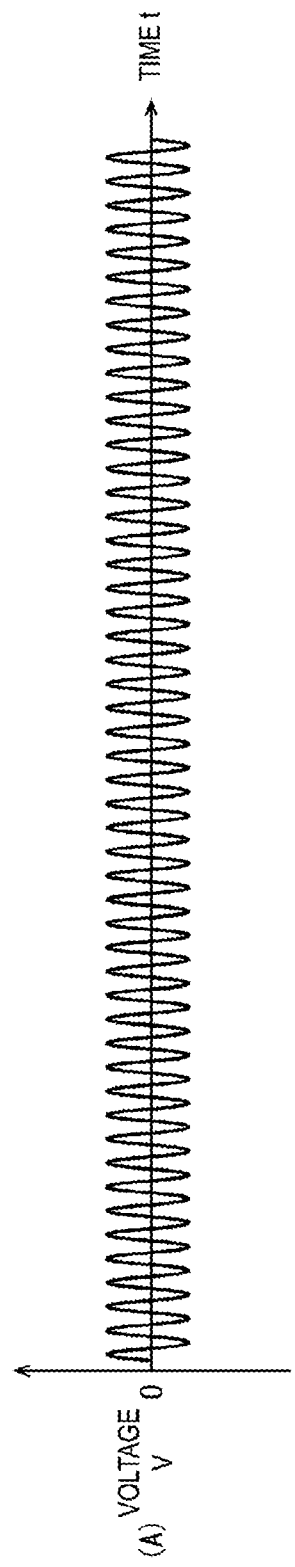
FIG. 6 is a waveform diagram for describing an example of impedance measurement in the electromedical device system illustrated in FIG. 5.
Figure 6:
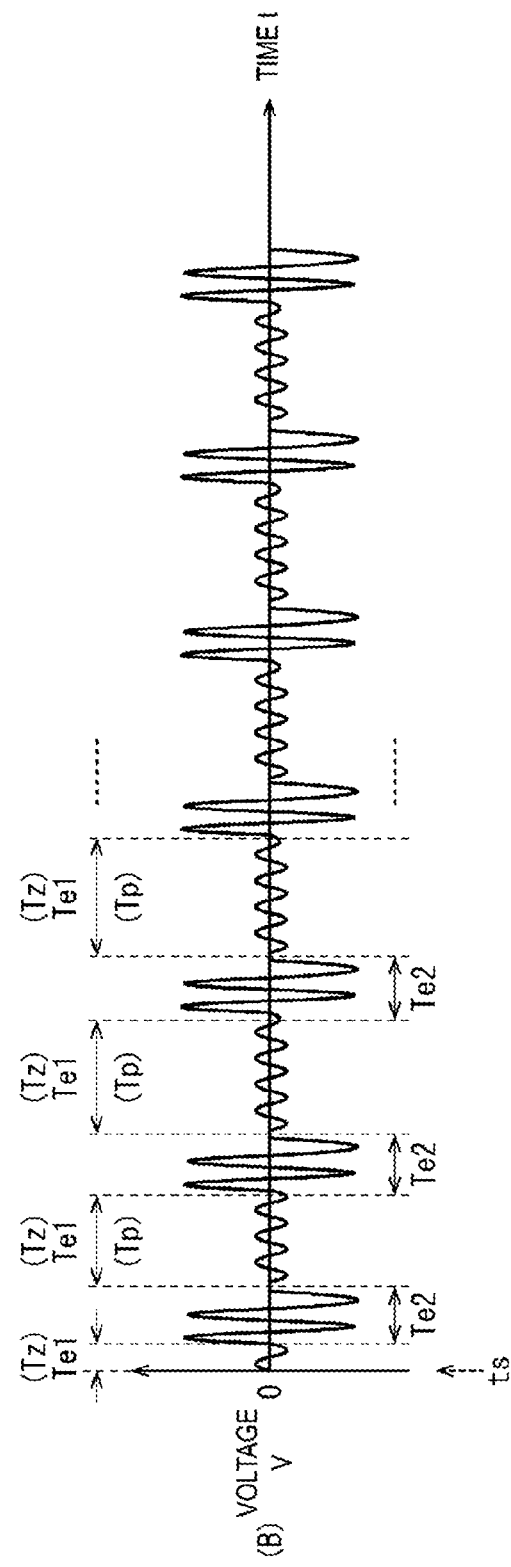

FIG. 6 is a waveform diagram for describing an example of impedance measurement in Modified Example 1. Specifically, FIG. 6A illustrates an example of change over time in the waveform of the voltage V during a coagulation mode using the electromedical device 1. FIG. 6B illustrates an example of change over time in the waveform of the voltage V during an incision mode using the electromedical device 1. Note that in FIGS. 6A and 6B, the horizontal axis indicates time t.

As described in the embodiment, in the power stop period Tn, the relay 341 is in an OFF state, and the supply of the power Pout from the power supply unit 32 is stopped. Therefore, the measurement (observation) of the impedance value Zm is not possible in the power stop period Tn before the start of the power supply.

In the normal RFA (coagulation mode) illustrated in FIG. 6A, the voltage V may be controlled so as to gradually reach the setting output during the RFA because the power supply time (energization period) is long (for example, 1 [s] or longer).

On the other hand, in the case of the incision mode illustrated in FIG. 6B, it is difficult to allow the voltage V to accurately reach the setting output in a short period of time because the power supply time is short (power is supplied by outputting a high voltage in a short period of time). Therefore, it can be said that it is desirable to obtain the impedance value Zm before the start of the main supply (main energization) of the power Pout by the high voltage output.

Thus, in Modified Example 1, in the power supply period Te, the measurement (pre-measurement) of the impedance value Zm by the preliminary supply (preliminary energization) of the power Pout is performed in a period (preliminary supply period Te1) before the start of the high voltage output to the energization target (the affected area of the patient 9) (main supply period Te2). In the preliminary supply period Te1, the supply (energization) of the power Pout itself is started, but a lower voltage than that in the main supply (high voltage output for the incision) is output.

Specifically, for example, as illustrated in FIG. 6B, in the incision mode, after the supply start timing ts, the preliminary supply and the main supply are alternately repeated in the order of the preliminary supply period Te1, the main supply period Te2, the preliminary supply period Te1, the main supply period Te2, and the like. That is, in the example of FIG. 6B, the high voltage output by the main supply is performed intermittently. In the first preliminary supply period Te1 (before the main supply) after the supply start timing ts, the measurement (pre-measurement) of the impedance value Zm by the preliminary supply with the low voltage output is performed (the first impedance measurement period Tz illustrated in FIG. 6B).

In addition, as illustrated in FIG. 6B, the impedance measurement may be performed even in the pause period Tp after the start of the main supply (between the intermittent main supply periods Te2). That is, even in the pause period Tp, the measurement of the impedance value Zm by the preliminary supply with the low voltage output may be performed (the second and subsequent impedance measurement periods Tz illustrated in FIG. 6B).

In this manner, in Modified Example 1, the measurement (pre-measurement) of the impedance value Zm by the preliminary supply (low voltage output) is performed in a period before the start of the high voltage output by the main supply in the power supply period Te, so that it is possible to achieve the following. That is, the pre-measurement is performed before the start of the main supply and the impedance value Zm is obtained in advance, so that the setting output can be accurately reached. As a result, in Modified Example 1, the convenience can be further improved as compared with the embodiment.

Additionally, in Modified Example 1, when the main supply is performed intermittently along the time axis, the measurement of the impedance value Zm by the preliminary supply is performed even in the pause period Tp after the start of the main supply, so that it is possible to achieve the following. That is, even after the start of the main supply, it is possible to use the pause period Tp of the main supply to obtain the impedance value Zm at the stage prior to resuming the main supply. As a result, it is possible to further improve convenience.

Note that the measurement of the impedance value Zm may be used to determine the contact of the electrode 111 on the electromedical device 1 with the affected area in the body of the patient 9, for example, as follows. That is, for example, it may be determined whether the electrode 111 is in contact with the affected area by comparing the impedance value Zm (for example, the impedance value Zm in the blood) when the electrode 111 is not in contact with the affected area (in the non-contact state) and the impedance value Zm during the measurement.

Modified Example 2

Figure 7:
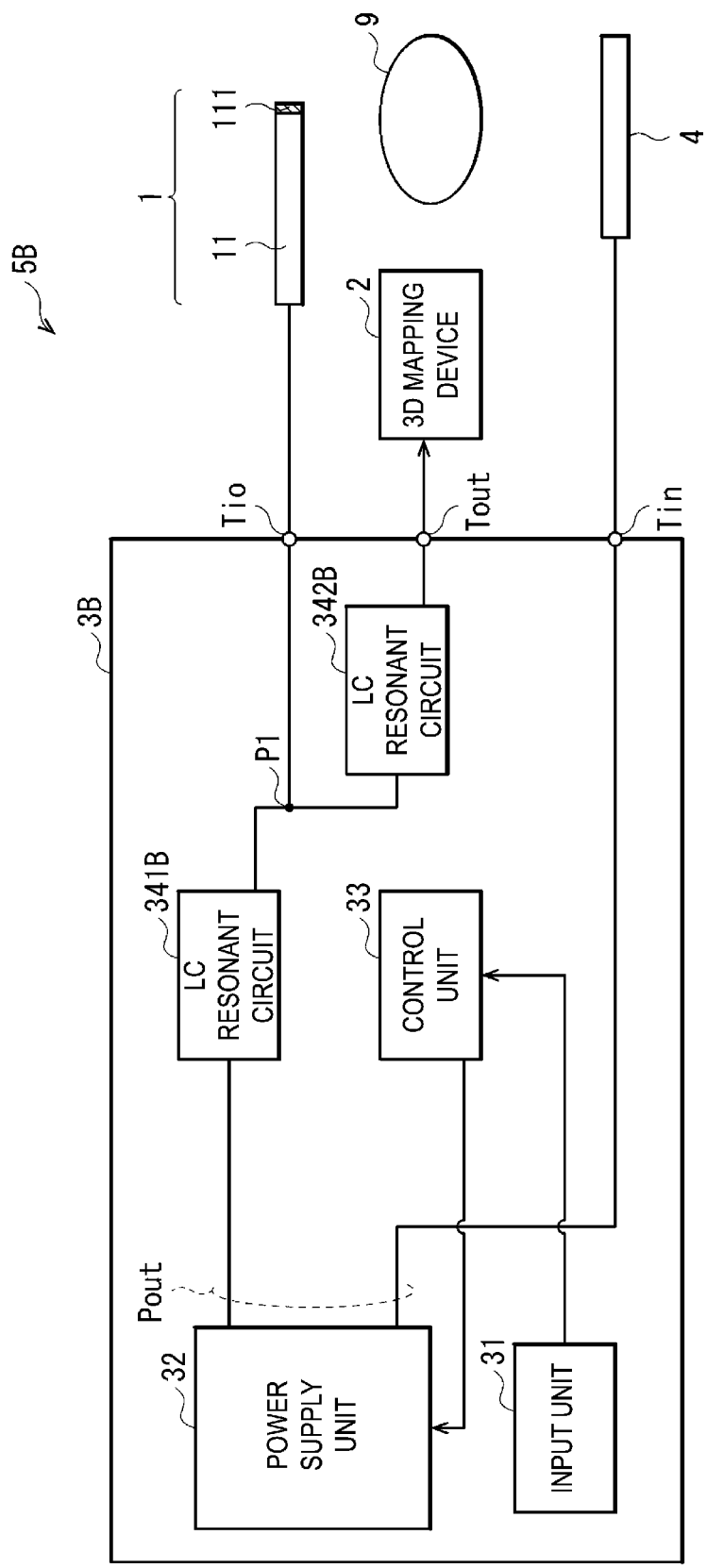
FIG. 7 is a block diagram schematically illustrating an overall configuration example of an electromedical device system according to Modified Example 2.

FIG. 7 is a block diagram schematically illustrating an overall configuration example of an electromedical device system 5B according to Modified Example 2. As to the electromedical device system 5B, a power supply device 3B is provided instead of the power supply device 3 in the electromedical device system 5 (FIG. 1) of the embodiment. The other configurations are the same.

As to the power supply device 3B, LC resonant circuits 341B and 342B are provided instead of the relays 341 and 342 in the power supply device 3 (FIG. 1). The other configurations are basically the same. Note that, since the LC resonant circuits 341B and 342B are provided instead of the relays 341 and 342, the control unit 33 in the power supply device 3B does not perform switching control of the relays 341 and 342 described above, unlike the control unit 33 in the power supply device 3.

Each of the LC resonant circuits 341B and 342B is a resonant circuit including a coil and a capacitor, and in particular, is an LC parallel resonant circuit in which the coil and the capacitor are connected in parallel with each other. Each of the LC resonant circuits 341B and 342B functions as a high impedance portion in a predetermined frequency band, and is configured such that the impedance state thereof transitions in accordance with the supply state of the power Pout described below (the state of energizing the energization target (the affected area of the patient 9) from the electromedical device 1). Specifically, the LC resonant circuit 341B has a frequency band including the frequency of the RF signal (power Pout) as a passband, and has a frequency band including the frequency of the three-dimensional mapping signal Sd as a non-passband. Conversely, the LC resonant circuit 342B has a frequency band including the frequency of the RF signal as a non-passband, and has a frequency band including the frequency of the three-dimensional mapping signal Sd as a passband. As a result, the impedance state of each of the LC resonant circuits 341B and 342B transitions between the low impedance state and the high impedance state in accordance with the supply state of the power Pout.

The LC resonant circuit 341B corresponds to a specific example of the "first impedance control unit" in the present disclosure. The LC resonant circuit 342B corresponds to a specific example of the "second impedance control unit" in the present disclosure.

FIG. 8 illustrates an example of a switching mode of the impedance state of each of the LC resonant circuits 341B and 342B.

As illustrated in FIG. 8, the impedance state of each of the LC resonant circuits 341B and 342B (the power supply state and the power stop state of the power supply device 3B) basically transitions in the same manner as in the case of the impedance state of each of the relays 341 and 342 described in the embodiment (FIG. 2).

In other words, in the power supply period Te (power supply state), the LC resonant circuit 341B passes the RF signal and is in the low impedance state. Furthermore, the LC resonant circuit 342B does not pass the RF signal and is in the high impedance state (a state in which the impedance is higher than the impedance in the low impedance state). In the power stop period Tn (power stop state), the LC resonant circuit 341B does not pass the three-dimensional mapping signal Sd and is in the high impedance state. Furthermore, the LC resonant circuit 342B passes the three-dimensional mapping signal Sd and is in the low impedance state.

In Modified Example 2, basically, the same effects can be obtained by the same operation as that of the embodiment.

Modified Example 3

Figure 9:
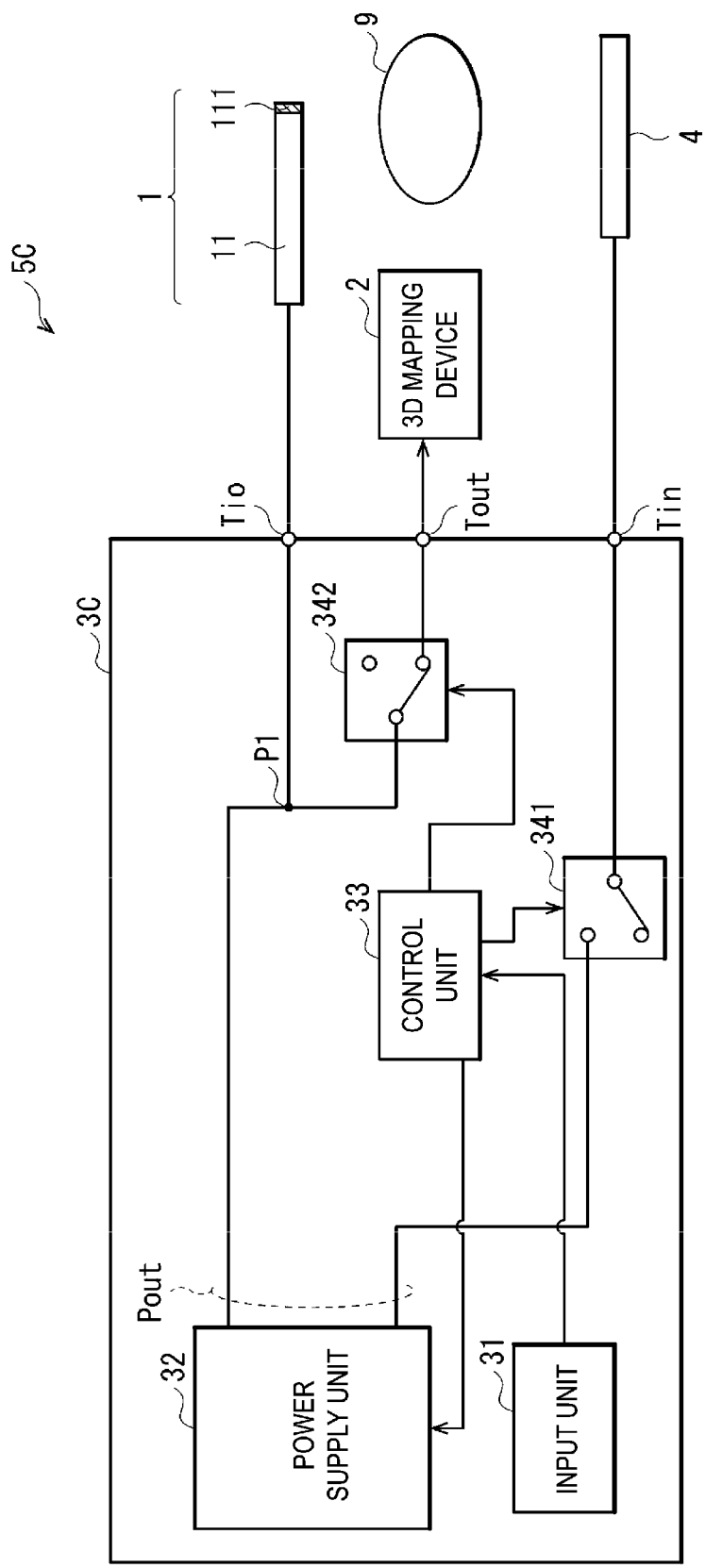
FIG. 9 is a block diagram schematically illustrating an overall configuration example of an electromedical device system according to Modified Example 3.

FIG. 9 is a block diagram schematically illustrating an overall configuration example of an electromedical device system 5C according to Modified Example 3. As to the electromedical device system 5C, a power supply device 3C is provided instead of the power supply device 3 in the electromedical device system 5 (FIG. 1) of the embodiment. The other configurations are the same.

As to the power supply device 3C, the arrangement position of the relay 341 is changed in the power supply device 3 (FIG. 1). The other configurations are the same. Specifically, in the power supply device 3, the relay 341 is disposed between the power supply unit 32 and the electromedical device 1 (in detail, between the power supply unit 32 and the connection point P1) on a path of the above-described circulation path of the power Pout, excluding the input path of the three-dimensional mapping signal Sd. In contrast, in the power supply device 3C, the relay 341 is disposed between the counter electrode plate 4 (another electrode) and the power supply unit 32 (in detail, between the input terminal Tin and the power supply unit 32) on a path of the circulation path of the power Pout, excluding the input path of the three-dimensional mapping signal Sd.

In Modified Example 3, basically, the same effects can be obtained by the same operation as that of the embodiment.

Note that in the power supply device 3B (FIG. 7) of Modified Example 2, the arrangement position of the LC resonant circuit 341B may be changed so as to be the same as the arrangement position of the relay 341 in the power supply device 3C. That is, the LC resonant circuit 341B may be disposed between the counter electrode plate 4 and the power supply unit 32 (between the input terminal Tin and the power supply unit 32) on a path of the circulation path of the power Pout, excluding the input path of the three-dimensional mapping signal Sd. In this case, basically, the same effects can be obtained by the same operation as that of Modified Example 2.

Modified Examples 4 and 5

Figure 10:
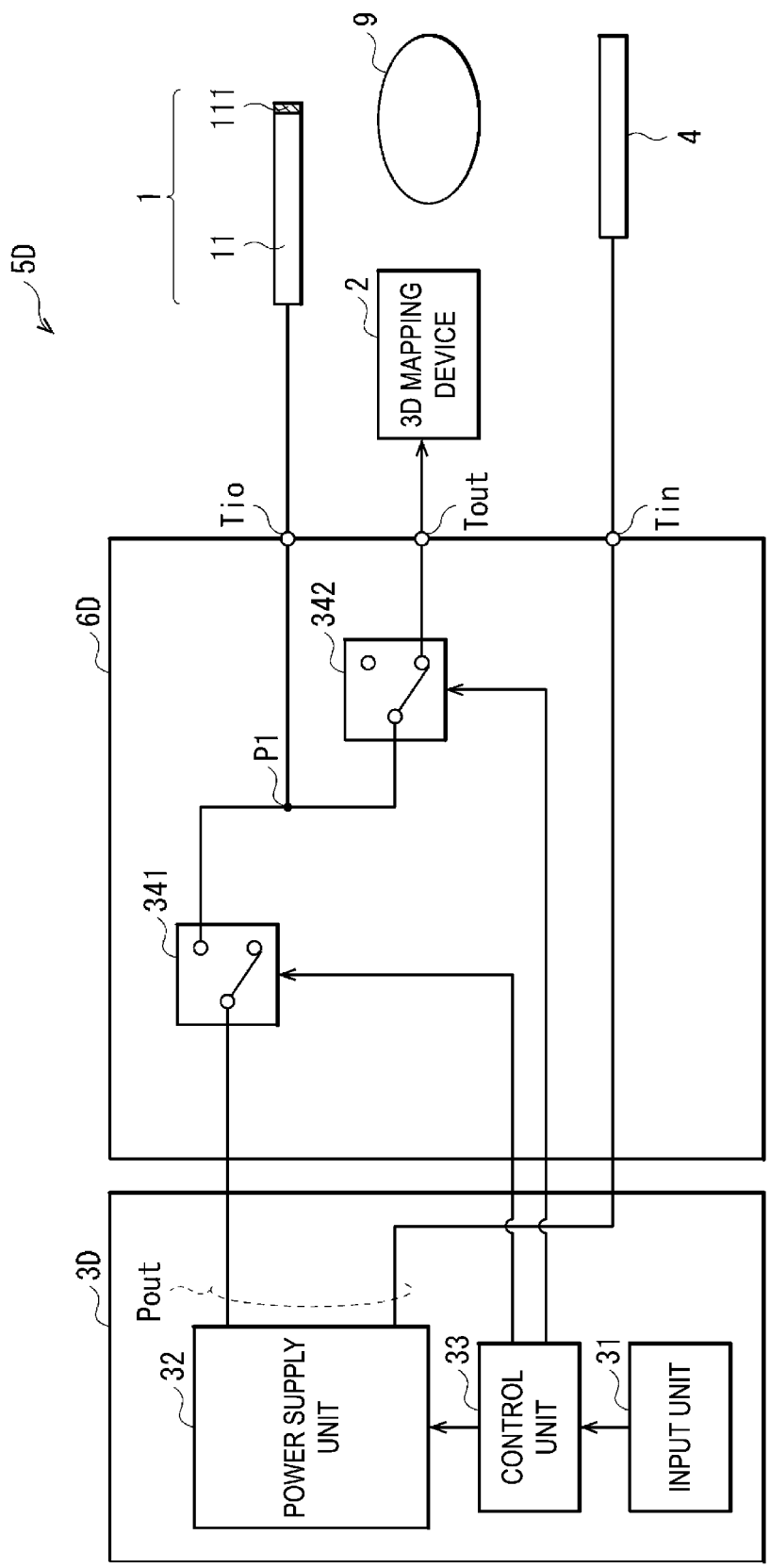
FIG. 10 is a block diagram schematically illustrating an overall configuration example of an electromedical device system according to Modified Example 4.
Figure 11:
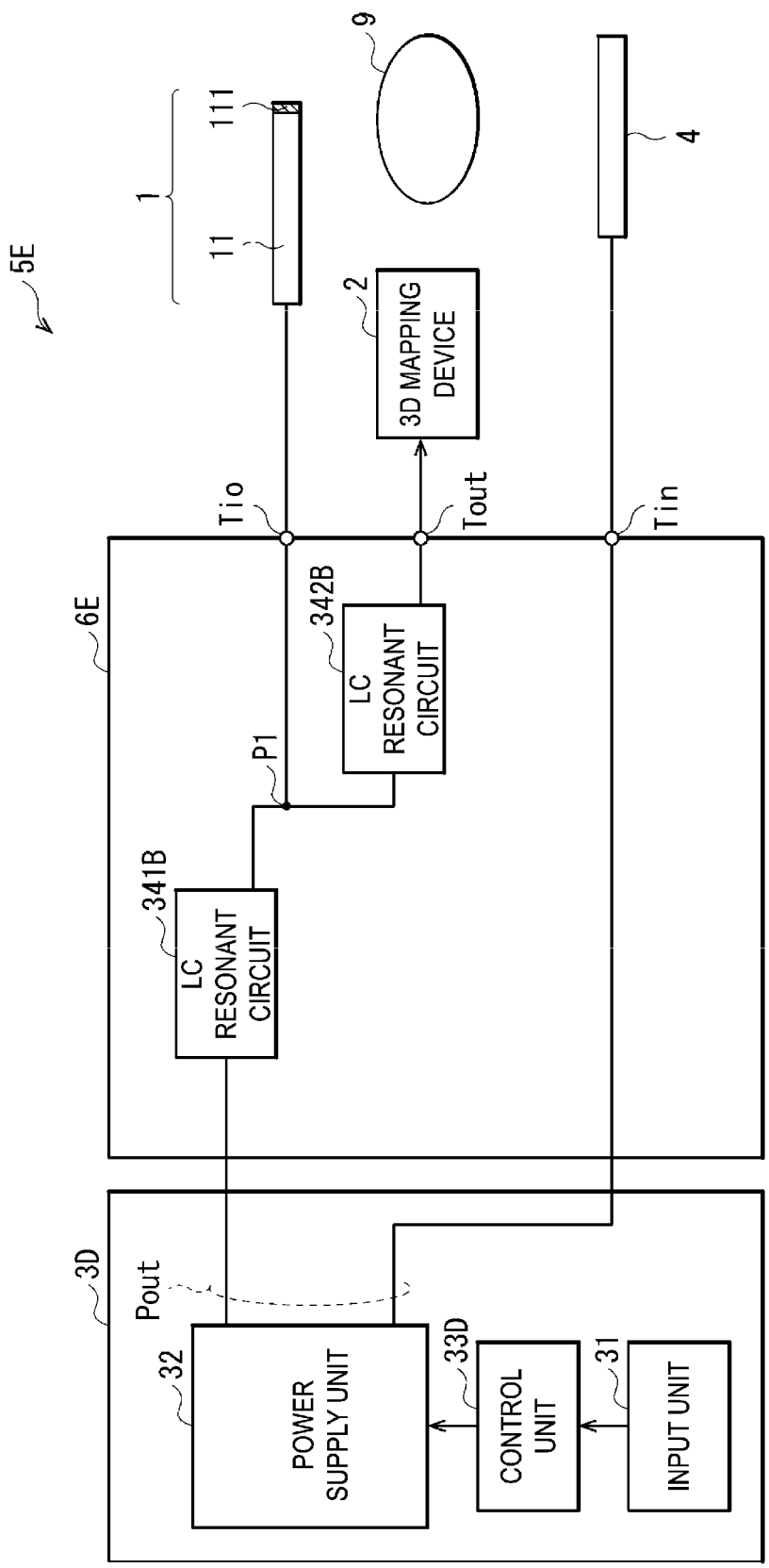
FIG. 11 is a block diagram schematically illustrating an overall configuration example of an electromedical device system according to Modified Example 5.

FIG. 10 is a block diagram schematically illustrating an overall configuration example of an electromedical device system 5D according to Modified Example 4. FIG. 11 is a block diagram schematically illustrating an overall configuration example of an electromedical device system 5E according to Modified Example 5.

As to the electromedical device system 5D, a power supply device 3D is provided instead of the power supply device 3 and a relay device 6D is further provided in the electromedical device system 5 (FIG. 1) of the embodiment. The other configurations are the same. As to the electromedical device system 5E, a power supply device 3D is provided instead of the power supply device 3 and a relay device 6E is further provided in the electromedical device system 5 (FIG. 1) of the embodiment. The other configurations are the same.

As to the power supply device 3D illustrated in FIG. 10, the relays 341 and 342 are omitted (not provided) in the power supply device 3 (FIG. 1). The other configurations are the same. As to the power supply device 3D illustrated in FIG. 11, a control unit 33D is provided instead of the control unit 33 and the relays 341 and 342 are omitted (not provided) in the power supply device 3 (FIG. 1). The other configurations are the same. The control unit 33D does not perform switching control of the relays 341 and 342 described above, unlike the control unit 33.

The relay device 6D is a device that relays between the electromedical device 1 and the power supply device 3D, as illustrated in FIG. 10. The relay device 6D includes relays 341 and 342 provided in the power supply device 3 (FIG. 1). The arrangement positions of the relays 341 and 342 in the relay device 6D are basically the same as the arrangement positions (FIG. 1) of the relays 341 and 342 in the power supply device 3.

As illustrated in FIG. 11, a relay device 6E is a device that relays between the electromedical device 1 and the power supply device 3D. The relay device 6E includes the LC resonant circuits 341B and 342B provided in the power supply device 3B (FIG. 7). The arrangement positions of the LC resonant circuits 341B and 342B in the relay device 6E are basically the same as the arrangement positions (FIG. 7) of the LC resonant circuits 341B and 342B in the power supply device 3B.

In this manner, as to the electromedical device systems 5D and 5E of Modified Examples 4 and 5, the relays 341 and 342 and the LC resonant circuits 341B and 342B are disposed in the relay devices 6D and 6E instead of the power supply devices 3 and 3B, respectively.

In Modified Examples 4 and 5, basically, the same effects can be obtained by the same operation as that of the embodiment and Modified Example 2.

3. OTHER MODIFIED EXAMPLES

Although the present disclosure has been described above with reference to the embodiment and the several modified examples, the present disclosure is not limited to the embodiment and the like, and various modifications are possible.

For example, in the above-described embodiment and the like, the overall configuration of the electromedical device system has been specifically described, but it is not always necessary to include all the devices, and other devices may be further included. The values, ranges, magnitude relations, and the like of various parameters described in the above-described embodiment and the like are not limited to those described in the above-described embodiment and the like, and may be other values, ranges, magnitude relations, and the like.

In the above-described embodiment and the like, an ablation device (ablation system) has been mainly described as a specific example of the electromedical device (electromedical device system), but the present disclosure is not limited to this example, and other electromedical devices (electromedical device systems) may be applied. The ablation device may be an ablation device that performs ablation using another electromagnetic wave such as a microwave or a high voltage pulse.

In the above-described embodiment and the like, an example of a monopolar type in which ablation is performed between the one electrode on the electromedical device and the counter electrode plate (another electrode) has been described, but the present disclosure is not limited to this example. That is, for example, a monopolar type in which a treatment or the like is performed between a plurality of electrodes on an electromedical device and a counter electrode plate (another electrode) may be used. Also, for example, a bipolar type in which a treatment or the like is performed between a plurality of electrodes on an electromedical device may be used.

In the above-described embodiment and the like, examples of the configuration (relay or LC resonant circuit) and arrangement position of the impedance control unit have been specifically described, but the present disclosure is not limited to these examples. In other words, the configuration and arrangement position of the impedance control unit may be another example different from the above-described embodiment and the like.

In the above-described embodiment and the like, the 3D mapping device that outputs the three-dimensional mapping signal as an electrical signal to the outside has been described as a specific example of another device to which the electrical signal obtained in the electromedical device is input, but the present disclosure is not limited to this example. That is, the example of the electrical signal is not limited to the three-dimensional mapping signal, and may be, for example, a two-dimensional mapping signal, or another electrical signal other than the mapping signal. The other device (output device) that outputs the electrical signal may be, for example, an output device, other than the mapping device (display device), which outputs voice or characters.

In the above-described embodiment and the like, the transition mode of the impedance state (switching control operation by the control unit), and the impedance measurement operation and the like in the impedance control unit (relay or LC resonant circuit) have been specifically described. However, the methods for these transition modes (switching control operation), measurement operations, and the like are not limited to the methods described in the embodiment and the like. That is, for example, the configuration of the relay is not limited to the double-pole double-throw relay, and may be a relay having a different number of poles, a single-throw relay, a semiconductor relay, or the like.

The series of processes described in the above-described embodiment and the like may be performed by hardware (circuit) or software (program). When the series of processes are done by software, the software includes a group of programs for causing a computer to execute each function. Each program may be used by being preliminarily incorporated in the computer, for example, or may be installed and used in the computer from a network or a recording medium.

The various examples described so far may be applied in any combination.

Note that the effects described in the present specification are mere examples and effects of the present disclosure are not limited thereto. Other effects may be obtained.

The present disclosure may also have the following configuration.

(1)

A power supply device including a power supply unit that supplies power to an electromedical device, a first impedance control unit disposed on a path of a circulation path of the power between the power supply unit and the electromedical device, excluding an input path for inputting an electrical signal obtained in the electromedical device to another device, and a second impedance control unit disposed on the input path of a path between the power supply unit and the other device, wherein an impedance state of each of the first and second impedance control units transitions in accordance with a supply state of the power to the electromedical device.

(2)

The power supply device according to (1) described above, wherein in a supply period of the power, the first impedance control unit is in a low impedance state, and the second impedance control unit is in a high impedance state, the high impedance state being a state in which an impedance is higher than an impedance in the low impedance state, and in a stop period of the power, the first impedance control unit is in the high impedance state, and the second impedance control unit is in the low impedance state.

(3)

The power supply device according to (1) or (2) described above, wherein the first impedance control unit includes a first relay, the second impedance control unit includes a second relay, and the power supply device further includes a relay control unit that performs switching control between ON states and OFF states of the first and second relays as the impedance states of the first and second impedance control units in accordance with the supply state of the power.

(4)

The power supply device according to (3) described above, wherein the relay control unit performs the switching control such that in a supply period of the power, the first relay is in the ON state as a low impedance state, and the second relay is in the OFF state as a high impedance state, the high impedance state being a state in which an impedance is higher than an impedance in the low impedance state, and the relay control unit performs the switching control such that in a stop period of the power, the first relay is in the OFF state as the high impedance state, and the second relay is in the ON state as the low impedance state.

(5)

The power supply device according to (3) or (4) described above, wherein in a supply period of the power, impedance measurement by preliminary supply of the power is performed in a period before start of high voltage output by main supply of the power, a voltage output in the preliminary supply of the power being lower than a voltage of the high voltage output.

(6)

The power supply device according to (5) described above, wherein the high voltage output by the main supply is performed intermittently along a time axis, and the impedance measurement by the preliminary supply is further performed in a pause period after the start of the high voltage output.

(7)

The power supply device according to (1) or (2) described above, wherein each of the first and second impedance control units includes an LC resonant circuit.

(8)

The power supply device according to any one of (1) to (7) described above, wherein the circulation path is a circulation path from the power supply unit to the power supply unit via an electrode on the electromedical device and another electrode.

(9)

The power supply device according to (8) described above, wherein the other electrode is a counter electrode plate, and the first impedance control unit is disposed between the power supply unit and the electromedical device or between the counter electrode plate and the power supply unit on a path of the circulation path excluding the input path.

(10)

The power supply device according to any one of (1) to (9) described above, wherein the other device is a mapping device that outputs a three-dimensional mapping signal as the electrical signal to an outside.

(11)

An electromedical device system including an electromedical device, and a power supply device that supplies power to the electromedical device, wherein the power supply device includes a power supply unit that outputs the power, a first impedance control unit disposed on a path of a circulation path of the power between the power supply unit and the electromedical device, excluding an input path for inputting an electrical signal obtained in the electromedical device to another device, and a second impedance control unit disposed on the input path of a path between the power supply unit and the other device, and an impedance state of each of the first and second impedance control units transitions in accordance with a supply state of the power to the electromedical device.

(12)

A relay device for relaying between an electromedical device and a power supply device that supplies power to the electromedical device, the relay device including a first impedance control unit disposed on a path of a circulation path of the power between the power supply device and the electromedical device, excluding an input path for inputting an electrical signal obtained in the electromedical device to another device, and a second impedance control unit disposed on the input path of a path between the power supply device and the other device, wherein an impedance state of each of the first and second impedance control units transitions in accordance with a supply state of the power to the electromedical device.

(13)

A power supply device including a first supply unit that supplies power from a power supply unit to an electromedical device, and a second supply unit that supplies an electrical signal obtained in the electromedical device to another device, wherein a transition is made, in accordance with a supply state of the power to the electromedical device, between a power supply state in which the other device is electrically separated from the first supply unit and the power is supplied to the first supply unit and a power stop state in which the electrical signal is supplied to the second supply unit and the second supply unit is electrically separated from other portions.

(14)

A method of controlling a power supply device including a first supply unit that supplies power from a power supply unit to an electromedical device, and a second supply unit that supplies an electrical signal obtained in the electromedical device to another device, the method including: making a transition, in accordance with a supply state of the power to the electromedical device, between a power supply state in which the other device is electrically separated from the first supply unit and the power is supplied to the first supply unit and a power stop state in which the electrical signal is supplied to the second supply unit and the second supply unit is electrically separated from other portions.

REFERENCE SIGNS LIST

1 Electromedical device
11 Device body
111 Electrode
2 3D mapping device
3, 3A to 3D Power supply device
31 Input unit
32 Power supply unit
33, 33D Control unit
341, 342 Relay
341B, 342B LC resonant circuit
351 Voltage measurement unit
352 Current measurement unit
4 Counter electrode plate
5, 5A to 5E Electromedical device system
6D, 6E Relay device
9 Patient
Pout Power
Tin Input terminal
Tout Output terminal
Tio Input/output terminal
P1 to P3 Connection point
Te Power supply period (energization period)
Tn Power stop period (non-energization period)
Rp Path
Sd Three-dimensional mapping signal
Sn Noise signal
Vm Measured voltage
Im Measured current
V Voltage
t Time
ts Supply start timing
Te1 Preliminary supply period
Te2 Main supply period
Tp Pause period
Tz Impedance measurement period

The invention claimed is:

1. A power supply device comprising:
a power supply unit configured to supply power to an electromedical device;
a first impedance control unit disposed on a path of a circulation path of the power between the power supply unit and the electromedical device, excluding an input path for inputting an electrical signal obtained in the electromedical device to another device; and
a second impedance control unit disposed on the input path of a path between the power supply unit and the other device, wherein
an impedance state of each of the first and second impedance control units transitions in accordance with a supply state of the power to the electromedical device.

2. The power supply device according to claim 1, wherein
in a supply period of the power, the first impedance control unit is in a low impedance state, and the second impedance control unit is in a high impedance state, the high impedance state being a state in which an impedance is higher than an impedance in the low impedance state, and
in a stop period of the power, the first impedance control unit is in the high impedance state, and the second impedance control unit is in the low impedance state.

3. The power supply device according to claim 1, wherein
the first impedance control unit includes a first relay,
the second impedance control unit includes a second relay, and
the power supply device further includes a relay control unit configured to perform switching control between ON states and OFF states of the first and second relays as the impedance states of the first and second impedance control units in accordance with the supply state of the power.

4. The power supply device according to claim 3, wherein
the relay control unit performs the switching control such that in a supply period of the power,
the first relay is in the ON state as a low impedance state, and the second relay is in the OFF state as a high impedance state, the high impedance state being a state in which an impedance is higher than an impedance in the low impedance state, and
the relay control unit performs the switching control such that in a stop period of the power, the first relay is in the OFF state as the high impedance state, and the second relay is in the ON state as the low impedance state.

5. The power supply device according to claim 3, wherein
in a supply period of the power, impedance measurement by preliminary supply of the power is performed in a period before start of high voltage output by main supply of the power, a voltage output in the preliminary supply of the power being lower than a voltage of the high voltage output.

6. The power supply device according to claim 5, wherein
the high voltage output by the main supply is performed intermittently along a time axis, and
the impedance measurement by the preliminary supply is further performed in a pause period after the start of the high voltage output.

7. The power supply device according to claim 1, wherein
each of the first and second impedance control units includes an LC resonant circuit.

8. The power supply device according to claim 1, wherein
the circulation path is a circulation path from the power supply unit to the power supply unit via an electrode on the electromedical device and another electrode.

9. The power supply device according to claim 8, wherein the other electrode is a counter electrode plate, and
the first impedance control unit is disposed between the power supply unit and the electromedical device or between the counter electrode plate and the power supply unit on a path of the circulation path excluding the input path.

10. The power supply device according to claim 1, wherein
the other device is a mapping device configured to output a three-dimensional mapping signal as the electrical signal to an outside.

11. An electromedical device system comprising:
an electromedical device; and
a power supply device configured to supply power to the electromedical device, wherein the power supply device includes
a power supply unit configured to output the power,
a first impedance control unit disposed on a path of a circulation path of the power between the power supply unit and the electromedical device, excluding an input path for inputting an electrical signal obtained in the electromedical device to another device, and
a second impedance control unit disposed on the input path of a path between the power supply unit and the other device, and
an impedance state of each of the first and second impedance control units transitions in accordance with a supply state of the power to the electromedical device.

12. A relay device for relaying between an electromedical device and a power supply device configured to supply power to the electromedical device, the relay device comprising:
a first impedance control unit disposed on a path of a circulation path of the power between the power supply device and the electromedical device, excluding an input path for inputting an electrical signal obtained in the electromedical device to another device; and
a second impedance control unit disposed on the input path of a path between the power supply device and the other device, wherein
an impedance state of each of the first and second impedance control units transitions in accordance with a supply state of the power to the electromedical device.

13. A power supply device comprising:
a first supply unit configured to supply power from a power supply unit to an electromedical device; and
a second supply unit configured to supply an electrical signal obtained in the electromedical device to another device, wherein
a transition is made, in accordance with a supply state of the power to the electromedical device, between a power supply state in which the other device is electrically separated from the first supply unit and the power is supplied to the first supply unit and a power stop state in which the electrical signal is supplied to the second supply unit and the second supply unit is electrically separated from other portions.

14. A method of controlling a power supply device including a first supply unit configured to supply power from a power supply unit to an electromedical device, and a second supply unit configured to supply an electrical signal obtained in the electromedical device to another device, the method comprising:
making a transition, in accordance with a supply state of the power to the electromedical device, between a power supply state in which the other device is electrically separated from the first supply unit and the power is supplied to the first supply unit and a power stop state in which the electrical signal is supplied to the second supply unit and the second supply unit is electrically separated from other portions.

* * * * *